(12) United States Patent
Varner et al.

(10) Patent No.: US 7,485,113 B2
(45) Date of Patent: Feb. 3, 2009

(54) METHOD FOR DRUG DELIVERY THROUGH THE VITREOUS HUMOR

(75) Inventors: Signe Erickson Varner, Los Angeles, CA (US); Eugene Dejuan, Jr., La Canada, CA (US); Terry Harrison Shelley, Hampstead, MD (US)

(73) Assignee: Johns Hopkins University, Baltimore, MD (US)

( * ) Notice: Subject to any disclaimer, the term of this patent is extended or adjusted under 35 U.S.C. 154(b) by 177 days.

(21) Appl. No.: 09/888,079

(22) Filed: Jun. 22, 2001

(65) Prior Publication Data
US 2002/0198511 A1    Dec. 26, 2002

(51) Int. Cl.
A61M 31/00    (2006.01)

(52) U.S. Cl. .................... 604/521; 604/506

(58) Field of Classification Search ............. 604/158, 604/506, 290, 294, 264, 272, 161, 521, 500
See application file for complete search history.

(56) References Cited

U.S. PATENT DOCUMENTS

| | | | |
|---|---|---|---|
| 3,598,119 A | 8/1971 | White ............... 128/215 |
| 3,659,610 A | 5/1972 | Climber ............ 128/347 |
| 4,002,169 A * | 1/1977 | Cupler, II .......... 604/22 |
| 4,645,491 A | 2/1987 | Evans ............... 604/158 |
| 4,710,171 A | 12/1987 | Rosenberg ......... 604/117 |
| 4,781,691 A | 11/1988 | Gross ............... 604/164 |
| 4,869,717 A * | 9/1989 | Adair ............... 604/506 |
| 4,909,784 A | 3/1990 | Dubroff ............. 604/49 |
| 4,978,334 A | 12/1990 | Toye et al. .......... 604/51 |
| 5,273,530 A * | 12/1993 | del Cerro et al. .... 604/521 |
| 5,326,345 A | 7/1994 | Price, Jr. ........... 623/4 |
| 5,328,481 A | 7/1994 | Wang ............... 604/51 |
| 5,409,457 A | 4/1995 | del Cerro et al. |
| 5,487,725 A | 1/1996 | Peyman ............. 604/22 |
| 5,792,099 A | 8/1998 | DeCamp et al. ..... 604/51 |
| 5,827,236 A | 10/1998 | Takahashi .......... 604/240 |
| 5,871,470 A | 2/1999 | McWha ............. 604/158 |
| 5,989,262 A * | 11/1999 | Josephberg ......... 606/107 |
| 6,254,587 B1 | 7/2001 | Christ et al. ........ 604/521 |

(Continued)

FOREIGN PATENT DOCUMENTS

EP    0 417 764 B1    6/1995

OTHER PUBLICATIONS

M.S. Silverman and S.E. Hughes, "Transplantation of Photoreceptors to Light-Damaged Retina." *Investigative Ophthalmology and Visual Science* 30:1684-1690 (1989).

(Continued)

*Primary Examiner*—Matthew F Desanto
(74) *Attorney, Agent, or Firm*—Edwards Angell Palmer & Dodge LLP; Peter F. Corless; Lisa Swiszcz Hazzard

(57) ABSTRACT

Devices and devices for the treatment of the eye are disclosed. Preferred devices of the invention include a piercing member that is inserted into the eye to create a pathway for a cannula. The cannula is slidably mounted to the piercing member and is adapted to reach a treatment site within the eye at which material is injected into and/or withdrawn from the eye. The outer diameter of the piercing member is small enough to allow for self-sealing of the insertion site of the device upon the device's withdrawal therefrom. Also disclosed are methods for the utilizing the devices to treat the eye.

51 Claims, 5 Drawing Sheets

U.S. PATENT DOCUMENTS

| | | | |
|---|---|---|---|
| 6,378,526 B1* | 4/2002 | Bowman et al. | 128/898 |
| 6,397,849 B1 | 6/2002 | Bowman et al. | 128/898 |
| 6,402,734 B1 | 6/2002 | Weiss | 604/521 |
| 6,428,553 B1* | 8/2002 | Trese | 606/161 |
| 6,537,253 B1 | 3/2003 | Haindl | 604/158 |
| 6,544,249 B1 | 4/2003 | Yu et al. | 604/521 |
| 6,579,256 B2 | 6/2003 | Hughes | 604/60 |
| 6,969,371 B2* | 11/2005 | Palasis et al. | 604/164.01 |
| 2002/0042652 A1* | 4/2002 | Peyman | 623/4.1 |
| 2002/0133184 A1* | 9/2002 | LoRusso | 606/167 |
| 2003/0073957 A1 | 4/2003 | Haindl | 604/164.02 |
| 2003/0158521 A1 | 8/2003 | Ameri | 604/117 |
| 2003/0171722 A1* | 9/2003 | Paques et al. | 604/264 |

OTHER PUBLICATIONS

R. Lopez, et al., "Transplantation of Cultured Rabbit Retinal Epithelium to Rabbit Retina Using A Closed-Eye Method." *Investigative Ophthalmology and Visual Science* 28:1131-1137 (1987).

V. Anand, et al., "Additional Transduction Events after Subretinal Readministration of Recombinant Adeno-Associated Virus." *Human Gene Therapy* 11 449-457 (2000).

J. Bennett, et al., "Adenovirus Vector-Mediated In Vivo Gene Transfer Into Adult Murine Retina." *Investigative Ophthalmology and Visual Science* 35:2535-2542 (1994).

Abstract of PubMed ID: 11437077; M.E. Verdugo et al.; Cell translation, (2001) 10(3) 317-27.

Abstract of PubMed ID: 9304644; A. Lowenstein et al.; Ophthalmic surgery and lasers, (Sep. 1997) 28(9) 774-5.

Abstract of PubMed ID: 8515951; K. J. Wald et al.; Ophthalmic surgery, (May 1993) 24(5) 336-8.

Abstract of PubMed ID: 2250851; E. A. Hansen et al.; Ophthalmic surgery (Oct. 1990) 21(120) 696-9.

* cited by examiner

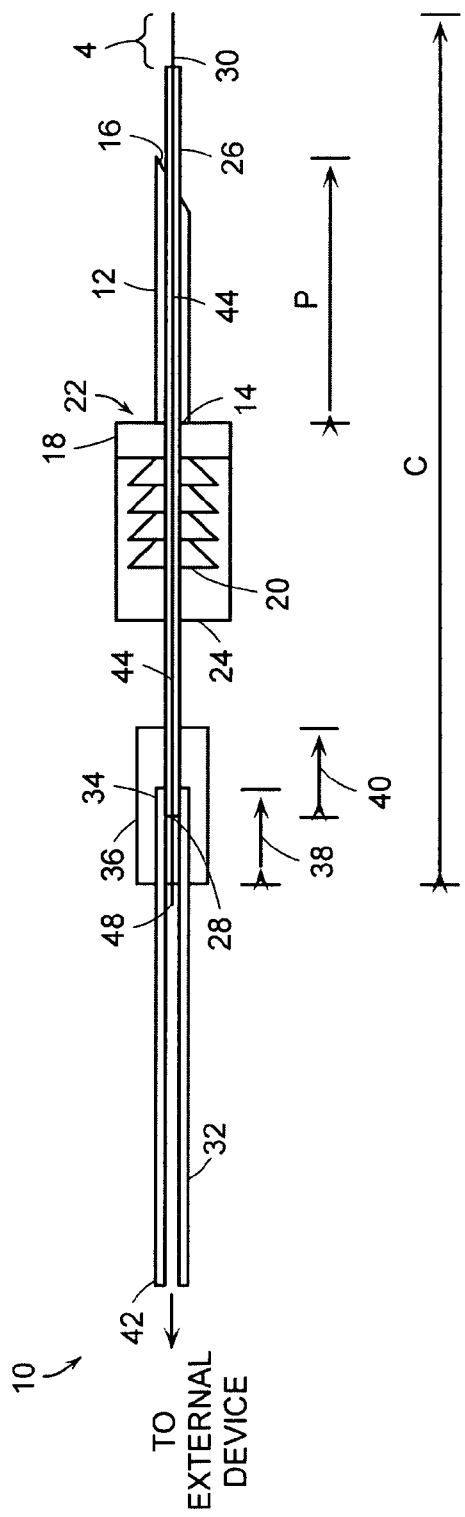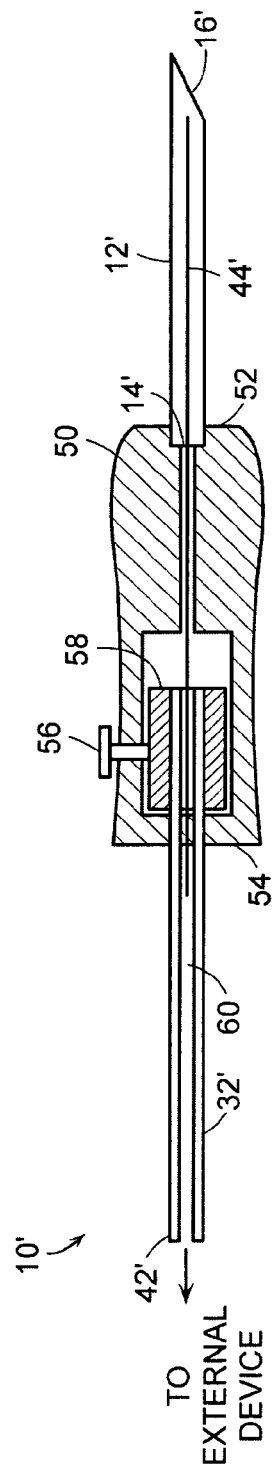

METHOD FOR DRUG DELIVERY THROUGH THE VITREOUS HUMOR

BACKGROUND OF THE INVENTION

1. Field of the Invention

The present invention relates generally to the delivery of medicaments, and more particularly, to devices and methods for delivering therapeutic agents directly to intraocular tissue and for withdrawing materials from within areas of the eye, such as the vitreous humor. These devices and methods are advantageous for many reasons, among which is that insertion of such a device into the eye necessitates forming an insertion site that is small enough to require no sutures to close, i.e., that is self-sealing, following post-treatment removal of the device.

2. Background

The delivery of drugs to the eye, especially the retina, presents many challenges, most of which are owed to the geometry, delicacy and/or behavior of the eye and its components.

For example, it is known in the art that ocular absorption of systemically administered pharmacological agents and medicaments is limited by the blood ocular barrier, i.e., tight junctions of the retinal pigment epithelium and vascular endothelial cells. And although high systemic doses of such medicaments and agents are capable of penetrating this barrier in relatively small amounts, a realistic risk of systemic toxicity accompanies such a course of treatment.

Topical delivery of pharmacological agents and medicaments, although involving fewer risks, has proven to be an equally ineffective treatment method. Not only do the complex hydrophobic/hydrophilic properties of the cornea and sclera hamper absorption of topically delivered agents, but data also indicates that it is not unusual for up to 85% of topically-applied agents to be removed by the eye's blink mechanism/reflex.

Intravitreal injection of a drug is an effective means of delivering the drug to the posterior segment of the eye in high concentrations, but it necessarily requires follow-up injections in order to maintain an adequate therapeutic concentration. This, in turn, presents problems because each additional intraocular injection carries with it a realistic risk of infection, hemorrhage and/or retinal detachment.

Moreover, even if intravitreal injection techniques were not otherwise problematic, such techniques have also proven inadequate for performing cell transplantation and gene therapy, which require, respectively, subretinal placement of cells and subretinal delivery of gene vectors.

Several specific prior art techniques for subretinal delivery of agents are known, e.g., those described in U.S. Pat. Nos. 5,273,530 and 5,409,457. Another such approach is discussed in *Investigative Ophthalmology and Visual Science* 30:1684 (1989), which details a microspatula device for administering cells to the eye through a trans-scleral or trans-corneal incision. Yet another instrument employed by those in the art is a glass pipette, which is used to replace cells in the retina by being introduced the eye anteriorly through an incision via the scleral route (*Investigative Ophthalmology and Visual Science* 28:1131(1987)).

Still other systems for subretinal drug injection, and for gene delivery are described in *Human Gene Therapy* 11:449 (2000) and *Investigative Ophthalmology and Visual Science* 35:2535 (1994). And yet another instrument known in the art to serve this purpose is a glass micro cannula.

A common feature of these techniques/instruments is that they necessarily require the creation of a surgical incision at the outset of a procedure, and/or the use of sutures following completion of the procedure. This, in turn, increases the duration, cost, and realistic risks of corneal ulceration, cataract formation, intraocular infection, and/or vitreous loss that accompany these procedures.

SUMMARY OF THE INVENTION

The present invention provides novel devices and methods for the delivery of agents to the eye. More particularly, the present invention relates to methods and devices for introducing materials (e.g., therapeutic agents/medicaments such as genes, proteins, cells, small molecule pharmaceuticals such as steroids and the like, and sterile solutions) into the subretinal space of the eye. The present device may also be used to effectuate the removal of intravitreal fluid from the eye.

The devices and methods of the invention also are employed to provide a localized deposit of a pharmaceutical agent within the eye, particularly subretinally. For instance a steroidal composition can be administered subretinally, wherein the steroid resides as a solid (e.g. from an initial suspension administration) and diffuses or otherwise is absorbed by the patient over time.

In an exemplary aspect of the present invention, the device includes a piercing member that has adequate sharpness to penetrate the sclera of a patient's eye. The piercing member may be connected to a handle or gripping element, which facilitates grasping of the device prior to and during use thereof.

The device further includes a cannula, which, in one aspect of the invention, is slidably disposed within a passageway defined within the device, and which, in another aspect of the invention, is connected to, and positioned within a rigid member disposed within this passageway. In the former aspect of the invention, the cannula is directly connected to a distal end of a quantity of tubing, while in the latter aspect, the rigid member is connected to the distal end of the tubing.

In both aspects of the invention, the proximal end of the quantity of tubing is attached to an externally located injection/removal device. This device is adapted to supply and/or withdraw fluid through the cannula, a distal end of which protrudes from the piercing element and into proximity of a treatment/target site within the eye.

In accordance with an exemplary method of the present invention, the piercing member is advanced into and through the sclera transconjunctively. The device is then advanced towards a target/treatment site (e.g. the retina) until the distal end of the cannula pierces the site.

Thereafter, the external device connected to the proximal end of the tubing is activated to either inject material (e.g., an agent/medicament) into the target site or to remove material therefrom. Upon completion of the injection and/or removal of material, the device is withdrawn from the target/treatment site, and then from the patient's eye by reversing the steps of its insertion.

During withdrawal of the device, the piercing member is removed from the eye. Preferably, the piercing member is small enough in size that the insertion site fashioned by the piercing member is self-sealing (i.e., requiring no sutures to close) following post-treatment removal of the piercing member therethrough.

In a preferred aspect of the invention, the device delivers an agent directly into the subretinal space of the patient's eye. In such an embodiment, the device is directed towards the retina such that the distal end of the cannula is advanced into, but not beyond, the subretinal space. Accuracy of placement of the device can be ensured/verified by techniques known in the art, e.g., by injecting agent through the cannula until the formation of a retinal detachment is observed. Injection of agent into this dome-shaped retinal detachment also enables the delivered agent to enjoy a prolonged residence time within the subretinal space. This, in turn, allows the agent to provide a greater therapeutic effect, without adversely affecting either intraocular pressure or neighboring retinal cells.

The present subretinal injection device is a self-contained system. Specifically, no separate surgical cannula systems are required during use of a device in accordance with the present invention. This allows for ease of handling of the device, which, coupled with the fact that the insertion site is self-sealing upon removal of the piercing member of the device, allows devices in accordance with the present invention to be uniquely suited for office-based procedures, which are comparatively less expensive, shorter in duration, and carry with them fewer risks than treatments necessitated by prior art systems and devices.

Moreover, because the insertion site is self-sealing upon removal of the piercing member, use of this device is a preferred treatment method as compared to currently known intraretinal transplantation procedures, which require the creation of a surgical incision prior to the treatment, and then the suturing of the incision following completion of the treatment. Specifically, in intraretinal transplantation techniques, a pars plana incision is required to insert a glass micropipette or similar instrument through the globe into the subretinal space. Upon completion of such techniques, scleral and conjunctival sutures, neither of which is required in accordance with the present invention, must be used to close the incision.

Moreover, once an eye has been entered, an operator can utilize the device of the present invention to treat multiple target sites simply by varying the angle of the entry of the device, thus avoiding the need for creation of multiple entry sites. Even in the event, however, that multiple entry sites were required, each entry site would be self-sealing as described above.

Further, because agents are delivered directly to the subretinal space by the device of the present invention, it follows that higher concentrations of the agent are delivered to the choroidal vessels and retinal pigment epithelial cells as compared to intravitreal injection and intraocular implants that introduce drugs into the vitreous humor. Injection into the subretinal space may also provide for a more sustained delivery of the agent/medicament to the retinal cells, thus avoiding a more rapid clearance rate from the vitreous. In addition, this type of local delivery may reduce the risk of elevated intraocular pressure associated with prior devices, which provide sustained drug delivery to the vitreous.

Other aspects of the invention are disclosed infra.

BRIEF DESCRIPTION OF THE DRAWINGS

FIG. 1 is a side view of an exemplary embodiment of a device in accordance with the present invention;

FIG. 2 is a side view of an alternate embodiment of the device of FIG. 1 in which the cannula is unsupported by a rigid member;

FIG. 3B 4 is a schematic view of the device of FIGS. 2/3A following piercing of the retina by the cannula of the device.

DETAILED DESCRIPTION OF THE INVENTION

Figure 3A:
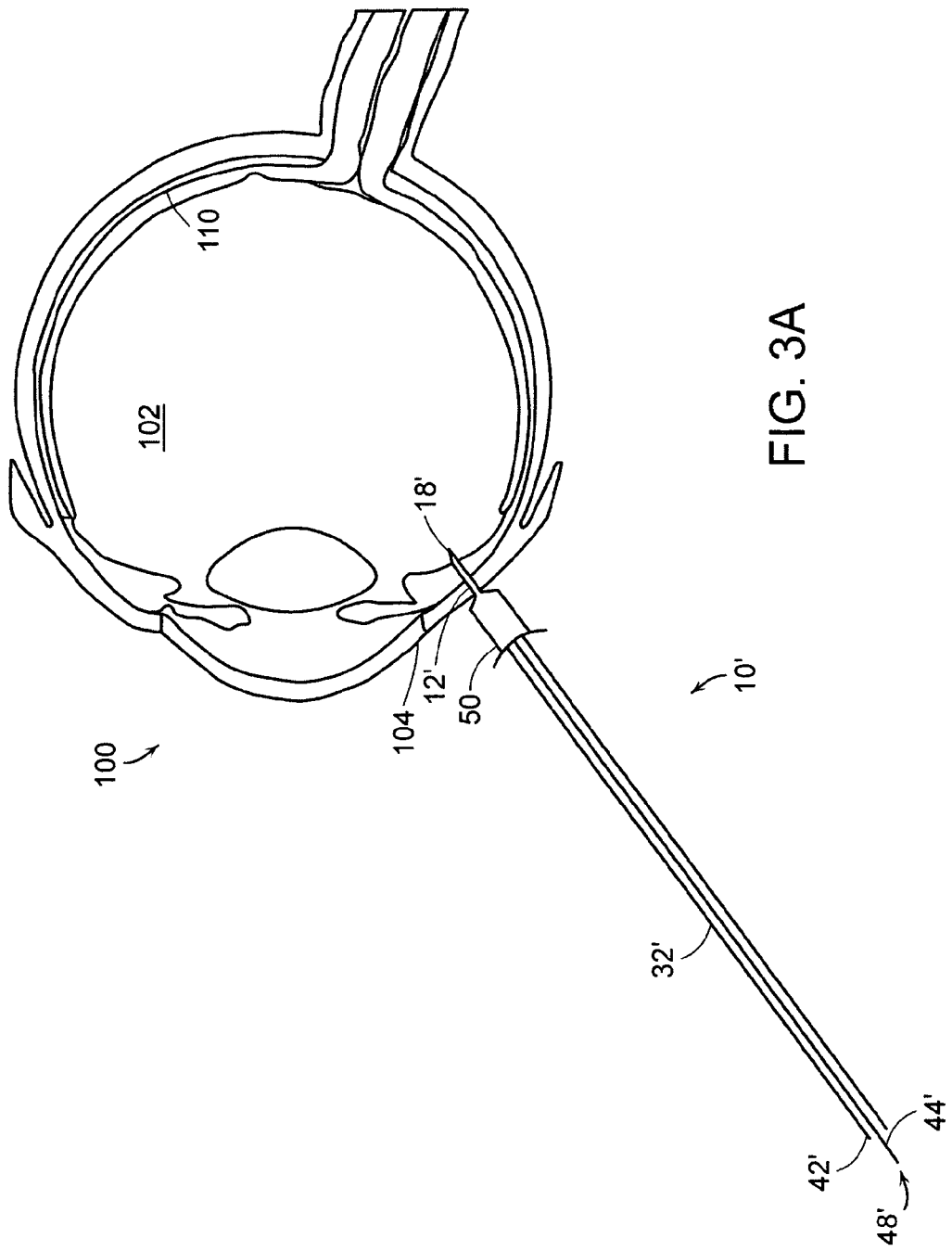
FIG. 3A is a schematic view of the device of FIG. 2 following puncture of the sclera of the eye by the piercing member of the device.

As stated above, new devices and methods are provided for delivery of agents to the eye.

Referring now to the various figures of the drawings, wherein like reference characters refer to like parts, there are depicted in FIGS. 1-4 various views of surgical devices 10, 10' in accordance with the present invention.

As shown in FIG. 1, a first exemplary embodiment of the device 10 of the present invention includes a piercing member 12, which has a proximal end 14 and a distal end 16, with a lumen defined therebetween. The distal end 16 of the piercing member 12 is pointed (e.g., beveled) to allow for the piercing member to pierce and penetrate a target/treatment site as will be described below.

In an exemplary embodiment of the present invention, the piercing member 12 has an outer diameter of about 25 gage (0.5 millimeter) or less and a length, P, in the range of about 6 millimeters to 25 millimeters, preferably in the range of about 15 millimeters to 20 millimeters.

The piercing member lumen should have a substantially constant diameter, which generally is in the range of about 0.152 millimeter to 0.305 millimeter.

The piercing member 12 may be made of a variety of biocompatible materials, including, but not limited to, polymers, metals and composites. Generally however, the piercing member 12 is made of a stainless steel.

The proximal end 14 of the piercing member 12 is connected, via a technique known in art (e.g., press fitting, and/or via an adhesive or an epoxy) to a first connection element 18.

The first connection element 18 has a proximal end 20 and a distal end 22 and a lumen defined therebetween. The first connection element lumen should have a diameter that is substantially identical to that of the piercing member lumen such that, upon connection of the proximal end 16 of the piercing member 12 to the distal end 22 of the first connection element 18, these lumen are substantially longitudinally aligned to create a fluid tight passageway.

The first connection element 18 may be made of a variety of biocompatible materials, including, but not limited to, polymers, metals and composites. Generally, the element 18 is made of titanium, stainless steel, nitinol or, preferably, delrin.

Optionally, but preferably, a seal 24 is connected to the first connection element 18, and substantially surrounds at least a portion of the first connection member lumen in order to further enhance the integrity of the fluid tight passageway. The seal 24 may be slidably connected to the first connection element 18 and/or may be connected via techniques known in the art, e.g., via an adhesive or an epoxy. The seal 24 can be made of a variety of materials, but is generally made of silicone.

The fluid tight passageway is sized to accommodate a rigid member 26, which adds physical stability to the device 10. The rigid member 26 has a proximal end 28 and a distal end 30, and a lumen defined therebetween. The distal end 30 of the rigid member 26 extends distal to the distal end 16 of the piercing member, while the proximal end 28 of the rigid member extends proximate to the seal 24.

A cannula 44 is disposed within the rigid member 26. Preferably, the cannula 44 is physically connected to the rigid member 26 (e.g., via adhesive, sealant, or epoxy or via other techniques known in the art) such that any distal-to-proximal or proximal-to-distal movement of the rigid member effects corresponding movement of the cannula, and such that any distal-to-proximal movement of the cannula effects corresponding movement of the rigid member.

The cannula 44 has a length, C, such that, when disposed within the rigid member 26, a distal portion 46 of the cannula is distal to the distal end 30 of the rigid member, while a proximal end 48 of the cannula extends proximal to the distal end 34 of the tubing 32.

It is understood, however, that the length, C, of the cannula 44 may be shorter or longer than depicted in FIG. 1. For example, the distal portion 46 of the cannula may extend further beyond the distal end 30 of the rigid member 26, and/or the proximal end 48 of the cannula may extend further proximately within the tubing or beyond the proximal end 42 of the tubing.

The length, C, of the cannula 44 is generally in the range of about 35 millimeters to 75 millimeters with its distal portion 46 generally having a length in the range of about 1 millimeter to 3 millimeters.

Generally, the outer diameter of the rigid member is about 28 gage (0.32 mm) or less, while the outer diameter of the cannula 44 in the range of about 38 gage (0.128 millimeter) to 45 gage (0.0457) millimeter.

Both the rigid member 26 and the cannula 44 can be made of a variety of biocompatible materials, including, but not limited to, polymers, metals and composites. In an exemplary embodiment of the present invention, the cannula 20 is made of polyimide tubing, while the rigid member 26 is made of either polyimide, titanium, nitinol, or, preferably, stainless steel.

As shown in FIG. 1, the rigid member 26 extends into a quantity of tubing 32 such that the proximal end 28 of the rigid member is proximal to the distal end 34 of the tubing. In an exemplary embodiment of the present invention, the tubing 32 and the rigid member 26 also are physically connected to each other (e.g., via an adhesive, a sealant, an epoxy or via other techniques known in the art) such that any distal-to-proximal or proximal-to-distal movement of the tubing effects corresponding movement of the rigid member (and, therefore, of the cannula as well), and such that any distal-to-proximal movement of either the rigid member or the cannula effects corresponding movement of the tubing.

Preferably, a second connection element 36 surrounds a distal portion 38 of the tubing 32 and a proximal portion 40 of the rigid member 26 in order to maintain the connection between the tubing and rigid member. The second connection element is connected to the tubing 32 and rigid member by a suitable technique known in the art, e.g., press fitting and/or via use of an adhesive or an epoxy.

The second connection element 36 may be made of a variety of biocompatible materials, including, but not limited to, polymers, metals and composites. Generally, the second connection element 36 is made of titanium, polyimide, nitinol, stainless steel or, preferably, delrin.

The tubing 32 includes a proximal end 42, which is in communication with an external supply or withdrawal device (not shown) either directly or via a connection element (e.g., a luer fitting). This connection allows for material (e.g., fluid, air, etc.) to be supplied into, or withdrawn from the tubing, each as will be discussed below.

Exemplary materials of which the tubing may be formed include, but are not limited to, a polymer, with preferred materials being silicon and polyimide.

Referring now to FIG. 2, it depicts an alternate embodiment of the device 10 of FIG. 1. The device 10' is similar in both structure and operation to the device 10 of FIG. 1, but includes a handle 50 and does not utilize a rigid member 26.

The device 10' of FIG. 2 includes a piercing member 12' substantially as described above except that the length of the piercing member is preferably in the range of about 22 millimeters to 30 millimeters.

The proximal end 14' of the piercing member 12' is connected to the distal end 52 of a handle 50, which has a proximal end 54 that is connected to a quantity of tubing 32'. By virtue of its connection to both the piercing member 12' and the tubing 32', the handle 50 is not only effective to facilitate initial and continued grasping of the device 10', but also to stabilize and provide support to the device 10'.

Each of the handle 50, the piercing member 12' and the tubing 32' has a lumen defined therebetween, thus defining a pathway between the distal end 16' of the piercing member and the proximal end 42' of the tubing.

A cannula is disposed within, and, preferably, connected to the lumen 60 defined within the tubing 32'. The tubing 32' and cannula 44' may be connected as is generally known in the art, e.g., via an adhesive, a sealant or an epoxy. By virtue of this connection, distal-to-proximal and proximal-to-distal movement of the tubing 32' will result in corresponding movement of the cannula 44', and vice versa.

The cannula 44' generally has identical length and outer diameter parameters to the cannula 44 of FIG. 1, and generally is made of the same material as well.

The handle 50 also includes an actuating element 56 that sits within a slot (not shown) or other opening. The actuating element 56 is in communication with a housing 58, which is in communication with the distal end 34' of the tubing 32' as shown in FIG. 2. By virtue of this arrangement, distal-to-proximal or proximal-to-distal movement of the actuating element 56 within the slot causes substantially corresponding movement of the housing, which, in turn, causes substantially corresponding movement of the tubing and, therefore, of the cannula 44' as well.

Exemplary materials from which the handle 50 and housing 58 may be made include, but are not limited to, biocompatible materials such as polymers (e.g., acetal, polyphenylene sulfide, polypropylene, ABS plastic), metals (e.g., stainless steel), and composites. Preferably, the handle 50 is made of acetal. The housing 58 may also be made of teflon or nylon. In an exemplary embodiment of the present invention, the handle 50 and the housing 58 are made of the same material.

The devices of FIGS. 1 and 2 are used to treat one or more target/treatment sites, each of which is generally located within an eye. Although the description of FIGS. 3A-B and 4A-B below refer to use of the device of FIG. 2, these descriptions also are applicable to use of the device of FIG. 1. Also, all common elements of the devices 10, 10' of FIGS. 1 and 2 will be referred to in these descriptions by their FIG. 2 reference numbers.

Referring now to FIG. 3A, in preparation for its use, the device 10' gains access to the vitreous humor 102 of a human eye 100. This occurs by placing enough pressure onto the device 10' such that the sharp distal end 18' of the piercing member 12' penetrates the sclera 104 of the eye 100, thus creating a continuous passageway (not shown) between the device and the vitreous humor 102 of the eye 100.

The piercing member 12' has a length, P (see FIG. 1) such that once its proximal end 16' is in contact with a portion of the outer periphery of the sclera 104, it is ensured that the distal end 18 of the piercing instrument is within the vitreous humor 102 of the eye 100. Once inserted as such, the piercing member 12' can be angled by gently tilting any portion of the device 10' that lies outside of the eye 100. This allows the device 10' to treat multiple target sites within the eye 38 without necessitating multiple, separate insertions of the device into the eye.

It is understood that although the process of inserting the piercing member 12' into the vitreous humor 102 is depicted in FIG. 3 as occurring while the cannula 44' is partially inserted within the device 10, the process may occur either with or without the cannula being entirely or partially within the device.

Figure 3B:
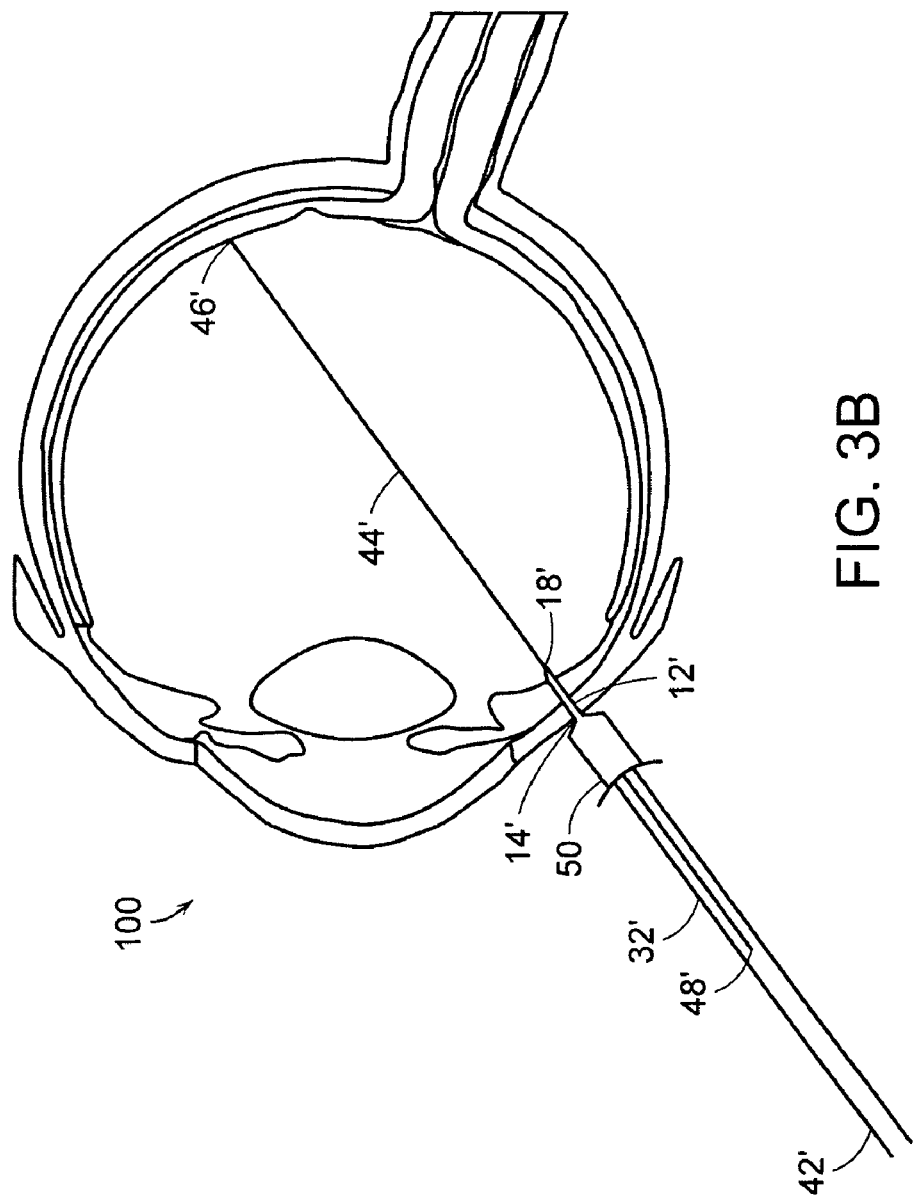
Figure 4A:
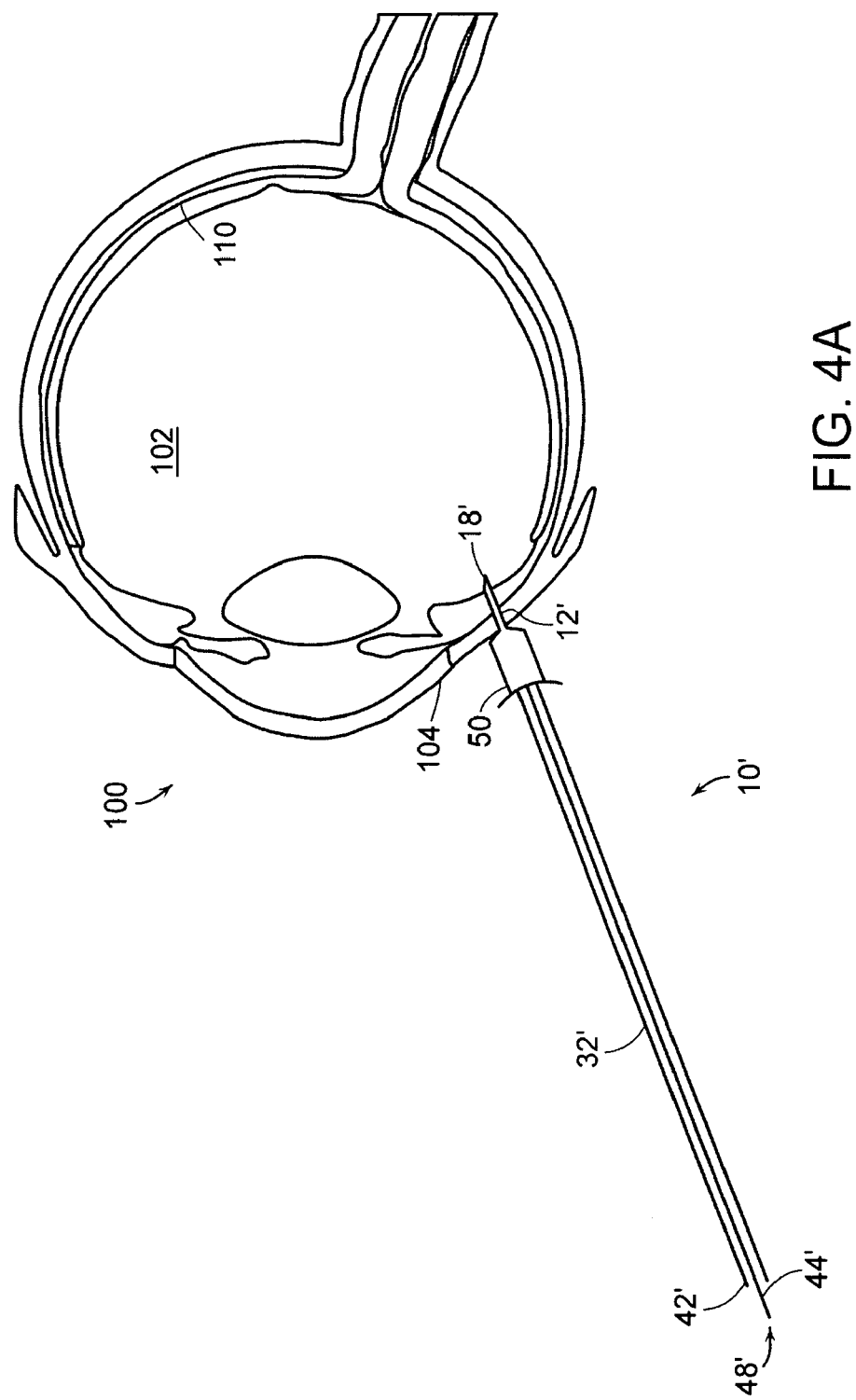
FIG. 4A is a schematic view of the device of FIGS. 2/3A depicting use of the device to treat multiple treatment sites by varying the angle of the portion of the device that lies outside of the eye.
Figure 4B:
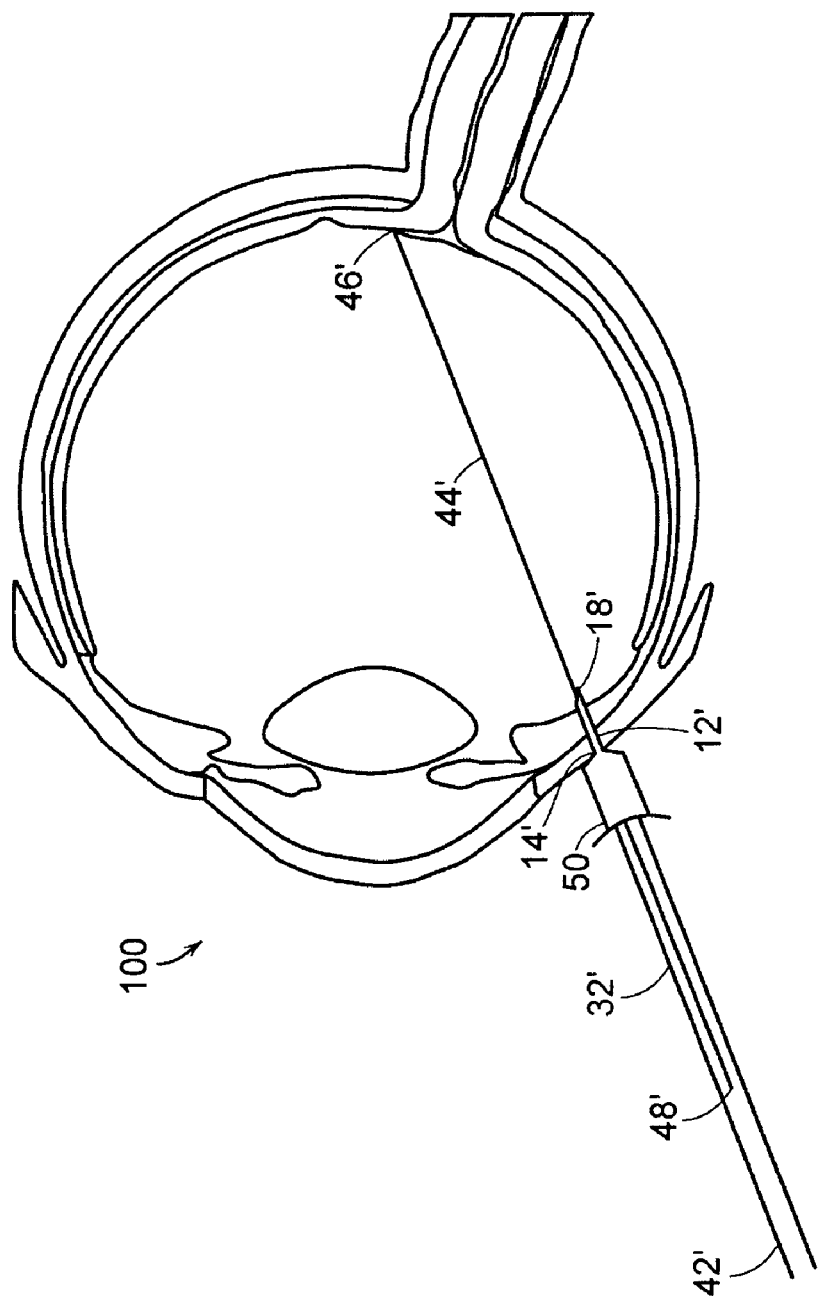
FIG. 4B is a schematic view of the device of FIGS. 2/4A following piercing of the retina by the cannula of the device.

Once a passageway into the eye 100 is created as such, the cannula 44' and attached tubing 32' (or, in the case of the device 10 of FIG. 1, the rigid member 26 with attached cannula 44 positioned therewithin) is advanced into and through the device 10' and to a treatment/target site. In FIGS. 3B and 4B, the target site is the retina 110 of the eye 100, but it is understood that the target site may be any portion of the eye.

In an embodiment in which the retina 110 is the target site, the cannula 44' is guided through the device 10' until a distal portion 46' of the cannula emerges from the guiding member 12', and into the vitreous humor 102.

The cannula 44' is further advanced within the eye 100 until the distal portion 46' of the cannula enters the retina 110. An operator of the device 10' is able to determine that the distal portion 46' of the cannula 44' has entered, but not traveled completely through, the retina 48 by virtue of techniques generally known in the art.

For example, once an operator estimates that the distal portion 46' of the cannula is approaching the retina, s/he can inject an agent through the cannula 44'. In order to simplify this estimation, the cannula 44' can include one or more markings that serve as visual and/or tactile indicators of the relative position of the cannula with respect to the retina. If, following this injection, the formation of a retinal detachment is observed, the operator can safely deduce that the distal portion 46' of the cannula 44' has entered, and still remains within, the retina 110 and can halt the distal advancement of the cannula.

Once proper positioning of the distal portion 46' of the cannula 44' at/within the treatment/target site 110 is ensured, the device may be utilized either to deliver or withdraw material from the eye 100. This occurs by activation of an externally located supply or withdrawal device (not shown) connected to the proximal end 42' of the tubing 32'. Preferably, this externally located device is connected to the tubing 32' by a connection device (not shown), e.g., a luer fitting or other connection device known in the art.

In an embodiment in which material is supplied to a treatment site, the material is infused into the proximal end 42' of the tubing 32' via an externally located supply device. The material travels through the tubing 32', wherein a quantity of the material is forced into the proximal end 48' of the cannula 44', through which it travels until it exits the distal portion 46' of the cannula.

In an embodiment in which material is withdrawn from a treatment site, an aspiration force is supplied through the tubing 32'. A sufficient amount of this force enters the proximal end 48' of the cannula 44' to enable material to be drawn into the distal portion 46' of the cannula 44' from the treatment site. This material then travels though the cannula 44', out its proximal end 48', into the tubing 32', and out the proximal end 42' of the tubing to an externally located collection device (not shown).

In an embodiment wherein material is delivered to the retina through an externally located supply device (e.g., a syringe), such material is generally a therapeutic agent or medicament, but may be any entirely or partially liquid-based or airborne material. Exemplary medicaments/agents include, but are not limited to, small molecule therapeutics, genes, proteins, or cells.

Among the uses for these agents/medicaments that are supplied to the retina 10 are for treatment of such problems/disorders as retinal detachment, vascular occlusions, proliferative retinopathy, diabetic retinopathy, inflammations such as uveitis, choroiditis and retinitis, degenerative disease, vascular diseases and various tumors including neoplasms.

It is understood that the amount of agent/medicament required to be delivered to the treatment site will vary depending on the treatment circumstances and will be readily calculable by one of ordinary skill in the art without undue experimentation.

In an exemplary embodiment in which materials are removed via the device 10', the treatment site may be the vitreous humor 102 of the eye 100. For example, portions of the vitreous humor 102 may be removed through the device 10' during a vitrectomy—a procedure often used to treat a variety of eye diseases, ocular injuries and complicated retinal detachments.

In accordance with an exemplary method of the present invention, the piercing member 12' is advanced into and through the sclera 104 (e.g., transconjunctively), thereby penetrating the eye 100. The cannula 44' (which is connected to the rigid member 26 in the embodiment of FIG. 1, and connected to the tubing 32' in the embodiment of FIG. 2) is then advanced through the device 10', then into and through the vitreous humor 102 to a target site, (e.g. the retina 110), such that the distal portion 46' of the cannula 44' pierces the target site.

An infusion or aspiration device (not shown) connected to the proximal end 42' of the tubing 32' is then activated to either inject material into the target site or to remove material therefrom as described above.

Upon completion of the injection and/or removal step, the cannula 44' is withdrawn from the eye 100 by reversing the steps of its insertion, after which the piercing member 12' is removed from the eye. Preferably, the piercing member has a small enough outer diameter, e.g., about 25 gage (0.4547 millimeters) or less, that the incision made by the piercing member to gain entry into and through the eye 100 is self-sealing, i.e., requiring no sutures for post-treatment closure.

In a particularly preferred embodiment, the device 10' is used to deliver an agent directly into the subretinal space 110 of a patient's eye 100. Once the distal portion 46' of the cannula 44' is properly positioned within the subretinal space 110, medicament is injected therein, thus raising a dome-shaped retinal detachment (not shown) that allows for the delivered medicament to enjoy a prolonged residence time within the subretinal space. This, in turn, allows the medicament to provide a greater therapeutic effect, without adversely affecting intraocular pressure or neighboring retinal cells, both of which are problems that plague procedures in which drugs are administered directly into the vitreous humor 102.

The present subretinal injection device 10' is a self-contained system, i.e., no additional devices other than those discussed in accordance with the embodiments described above must be employed during use of the device. Moreover, the insertion site of the piercing member 12' is self-sealing, also as discussed above.

These features of the present invention allow the device 10' to be uniquely suited to office-based procedures (i.e., procedures that are not required to take place in a hospital setting). Such office-based procedures are comparatively less expensive, shorter in duration, and carry with them less risk than treatments necessitated by prior art systems and devices.

Moreover, because the area of entry of the device 10' is self-sealing upon removal of the device, use of this device is a preferred treatment method as compared to intraretinal transplantation, which requires surgically opening the eye. Specifically, in intraretinal transplantation techniques, a pars plana incision is required to insert a glass micropipette or similar instrument through the globe and into the subretinal space. Upon completion of the procedure, scleral and conjunctival sutures are required to close the incision. As indicated above, this results in a prolonged procedure and/or an increased risk of infection, problems which are avoided due to the insertion site for the piercing member 12' of the present invention being self-sealing.

Another advantage of a device 10' of the present invention is that an operator may use it to treat multiple treatment sites simply by varying the angle of the portion of the device that lies outside of the eye 100, for example, as depicted in FIGS. 3A-4B, thus avoiding the need for creation of multiple entry sites. Even in the event, however, that multiple entry sites were required, each entry site would be self-sealing as described above.

Further, because the agents are delivered directly to the subretinal space by the device 10' of the present invention, it follows that higher concentrations of the agent/medicament are delivered to the choroidal vessels and retinal pigment epithelial cells as compared to intravitreal injection and intraocular implants that introduce drugs into the vitreous humor. Moreover, the local delivery accomplished by the present device 10' and methods may also reduce the risk of elevated intraocular pressure associated with prior devices that provide sustained drug delivery to the vitreous humor.

The present device further provides a method for direct intraretinal injection of therapeutics. Properly designed formulations delivered in such a manner result in sustained local delivery to retinal tissues, while reducing the risk of affecting intraocular pressure that accompanies intravitreal implants.

The present invention also includes kits (not shown) that comprise one or more devices 10' in accordance with the invention. Such kits also may include equipment (e.g., one or more containers, and aerosol canisters) for use with the device(s) 10', and/or written instructions for use of the device (s) and/or the equipment.

The invention also includes kits that comprise one or more devices of the invention, preferably packaged in sterile condition. Kits of the invention may include, e.g., one or more piercing members with contained cannula, preferably packaged in sterile condition, and/or written instructions for use of the device and other components of the kit.

The foregoing description of the invention is merely illustrative thereof, and it is understood that variations and modifications can be effected without departing from the scope or spirit of the invention as set forth in the following claims. All documents mentioned herein are incorporated by reference herein in their entirety.

What is claimed is:

1. A method for treating an eye comprising:
   inserting into an eye a device comprising a piercing member having a proximal end and a distal end and a lumen defined therebetween along a longitudinal axis of the piercing member and a cannula slidably disposed within the lumen, wherein the step of inserting the device into the eye comprises penetrating the eye with the piercing member and advancing the piercing member through the eye transconjunctively until the distal end is within the vitreous humor of the eye;
   advancing the cannula through the piercing member lumen, through the vitreous humor, and towards a treatment site;
   piercing the treatment site with the cannula; and
   treating the eye by administering and/or aspirating material through the cannula.

2. The method of claim 1 wherein the step of treating the eye comprises administering a therapeutic agent to the eye through the cannula.

3. The method of claim 2 wherein a steroid is administered to the eye.

4. The method of claim 2 wherein a therapeutic agent is administered to the eye to treat retinal detachment, vascular occlusion, proliferative retinopathy, diabetic retinopathy inflammation, degenerative disease, vascular disease or a tumor.

5. The method of claim 2 wherein the cannula is positioned within subretinal space of the eye and a therapeutic agent is injected from the cannula into the subretinal space.

6. The method of claim 1 further comprising removing material from the eye with the device.

7. The method of claim 6 wherein intravitreal fluid is removed from the eye.

8. The method of claim 1 wherein the therapeutic agent is administered subretinally to the patient's eye.

9. The method of claim 1 wherein the maximum cross-sectional dimension of the piercing member is about 25 gauge or smaller.

10. The method of claim 1 wherein the cannula comprises a polymer.

11. The method of claim 1 wherein the outer diameter of the piercing member is small enough to allow the insertion site to self-seal following withdrawal of the piercing, member from the eye.

12. The method of claim 1 wherein the piercing member creates an opening in the eye that is self-sealing.

13. A method of treating an eye, comprising:
   piercing the eye with a piercing member and inserting the piercing member into the vitreous humor of the eye, the piercing member having a proximal end and a distal end and a lumen defined therebetween;
   angling the piercing member in any direction so as to guide the cannula to any treatment site within the eye;
   advancing a cannula through the piercing member lumen and beyond the distal end of the piercing member;
   guiding the cannula through the vitreous humor of the eye to the treatment site; and
   treating the treatment site.

14. The method of claim 13 wherein the treating comprises administering to the eye a therapeutic agent through the cannula.

15. The method of claim 14 wherein a steroid is administered to the eye.

16. The method of claim 14 wherein a therapeutic agent is administered to the eye to treat retinal detachment, vascular occlusion, proliferative retinopathy, diabetic retinopathy, inflammation, degenerative disease, vascular disease or a tumor.

17. The method of claim 14 wherein the therapeutic agent is administered subretinally in the eye.

18. The method of claim 14 wherein the cannula is positioned within subretinal space of the eye and a therapeutic agent is injected from the cannula into the subretinal space.

19. The method of claim 13 wherein the step of guiding the cannula to the treatment site comprises:
   advancing the cannula within the eye until the distal end of the cannula is within the treatment site.

20. The method of claim 13 or 19 wherein the step of treating the treatment site comprises:
supplying a medicament through the cannula and into the treatment site via the distal end of the cannula.

21. The method of claim 13 wherein the treating comprises removing material from the eye with the device.

22. The method of claim 21 wherein intravitreal fluid is removed from the eye.

23. The method of claim 13 wherein the medicament is selected from the group consisting of genes, proteins, cells, small molecule pharmaceuticals and sterile solutions.

24. The method of claim 13 wherein the step of treating the treatment site comprises withdrawing material from the treatment site into the distal end of the cannula.

25. The method of claim 13 wherein the step of piercing the eye with a piercing member comprises inserting the distal end of the piercing member into and through the eye's sclera.

26. The method of claim 13 wherein the treatment site is selected from the group consisting of the eye's retina and the eye's vitreous humor.

27. The method of claim 13 wherein the treatment site is the eye's retina and the step of treating the treatment site comprises:
injecting medicament through the cannula and under the retina such that a dome-shaped retinal detachment is formed.

28. The method of claim 13 wherein the outer diameter of the piercing member is about 25 gauge or smaller.

29. The method of claim 13 wherein the piercing member is inserted into the sclera of the eye.

30. The method of claim 13 wherein the piercing member is advanced transconjuctivally through the eye.

31. The method of claim 13 wherein the cannula comprises a polymer.

32. The method of claim 13 wherein the outer diameter of the piercing member is small enough to allow the insertion site to self-seal following withdrawal of the piercing member from the eye.

33. The method of claim 13 wherein the piercing member creates an opening in the eye that is self-sealing.

34. The method of claim 13 further comprising, after treating the treatment site, angling the piercing member to a different direction so as to guide the cannula towards a second treatment site; advancing the cannula to the second a treatment site; and treating the second treatment site.

35. A method for treating an eye comprising:
inserting into an eye a device comprising an outer member having a proximal end and a distal end, a cannula slidably disposed within the outer member along a longitudinal axis of the outer member, and a piercing member at the distal end of the outer member, wherein the step of inserting the device into the eye comprises
piercing the eye with the piercing member and advancing the piercing member and at least a portion of the outer member into the eye transconjunctively;
advancing the cannula through the outer member and beyond the distal end through the virteous humor of the eye to pierce the treatment site; and
treating the eye by administering and/or aspirating material through the cannula.

36. The method of claim 35 wherein the step of treating the eye comprises administering to the eye a therapeutic agent with the device.

37. The method of claim 36 wherein the therapeutic agent is administered through the cannula to the treatment site.

38. The method of claim 36 wherein a steroid is administered to the eye.

39. The method of claim 36 wherein a therapeutic agent is administered to the eye to treat retinal detachment, vascular occlusion, proliferative retinopathy, diabetic retinopathy, inflammation, degenerative disease, vascular disease or a tumor.

40. The method of claim 36 wherein the therapeutic agent is administered sub-retinally within the eye.

41. The method of claim 36 wherein the cannula is positioned within the subretinal space of the eye and a therapeutic agent is injected from the cannula into the subretinal space.

42. The method of claim 35 further comprising removing material from the eye with the device.

43. The method of claim 42 wherein intravitreal fluid is removed from the eye.

44. The method of claim 1 or 35, further comprising the step of angling the piercing member, after the piercing member is within the vitreous humor of the eye in any direction so as to guide the cannula to any treatment site within the eye.

45. The method of claim 44, wherein the piercing member is angled so as to treat multiple treatment sites with a single insertion of the piercing member into the eye.

46. The method of claim 35 wherein the device is inserted into the sclera of the eye.

47. The method of claim 35 wherein the device is advanced transconjunctivally through the eye.

48. The method of claim 35 wherein the cannula comprises a polymer.

49. The method of claim 35 wherein the outer diameter of the outer member is small enough to allow the insertion site to self-seal following withdrawal of the piercing member from the eye.

50. The method of claim 35 wherein the outer member outer diameter is about 25 gauge or less.

51. The method of claim 35 wherein the piercing member creates an opening in the eye that is self-sealing.

* * * * *